(12) United States Patent
Hong

(10) Patent No.: US 11,402,387 B2
(45) Date of Patent: Aug. 2, 2022

(54) SYSTEM AND METHOD FOR DETERMINING GLYCAN TOPOLOGY USING TANDEM MASS SPECTRA

(71) Applicant: BRANDEIS UNIVERSITY, Waltham, MA (US)

(72) Inventor: Pengyu Hong, Waltham, MA (US)

(73) Assignee: Brandeis University, Waltham, MA (US)

( * ) Notice: Subject to any disclaimer, the term of this patent is extended or adjusted under 35 U.S.C. 154(b) by 212 days.

(21) Appl. No.: 16/616,831

(22) PCT Filed: Jun. 1, 2018

(86) PCT No.: PCT/US2018/035649
§ 371 (c)(1),
(2) Date: Nov. 25, 2019

(87) PCT Pub. No.: WO2018/223025
PCT Pub. Date: Dec. 6, 2018

(65) Prior Publication Data
US 2020/0096518 A1    Mar. 26, 2020

Related U.S. Application Data

(60) Provisional application No. 62/513,495, filed on Jun. 1, 2017, provisional application No. 62/531,229, filed on Jul. 11, 2017.

(51) Int. Cl.
*G01N 33/68*    (2006.01)
*G16C 20/20*    (2019.01)
(Continued)

(52) U.S. Cl.
CPC ..... *G01N 33/6848* (2013.01); *G01N 33/6842* (2013.01); *G16B 15/00* (2019.02);
(Continued)

(58) Field of Classification Search
None
See application file for complete search history.

(56) References Cited

U.S. PATENT DOCUMENTS

2011/0137570 A1*  6/2011  Lapadula ............... C12Q 1/34
                                                    702/19
2015/0340213 A1   11/2015  Belov

FOREIGN PATENT DOCUMENTS

CN    106404883 A     2/2017
WO    2009154964 A2   12/2009

OTHER PUBLICATIONS

Saar-Tsechansky, M. et al. Handling Missing Values when Applying Classification Models, Journal of Machine Learning Research 8 (2007) 1625-1657 (Year: 2007).*

(Continued)

*Primary Examiner* — Xiaoyun R Xu
(74) *Attorney, Agent, or Firm* — Quarles & Brady LLP

(57) ABSTRACT

The method presented herein includes acquiring a mass spectrum of a molecule that includes mass spectrum peaks corresponding to a precursor ion and fragment ions. The method also includes identifying at least a portion of the fragment ions in the mass spectrum as corresponding to one or more monomer subunit ion of the precursor ion by appending one or more of the fragment ions to an inferable constituent to produce a topology building block. The topology building block is then stored in a candidate pool as corresponding to one or more of the monomer subunit ion if the combined mass of the inferable constituent and one or more of the fragment ions satisfy a first user-defined mass tolerance. One or more candidate topology of the precursor ion is then obtained by combining a plurality of the topology building blocks that satisfy a second user-defined mass tolerance for the precursor ion.

19 Claims, 9 Drawing Sheets

(51) Int. Cl.
  *H01J 49/00* (2006.01)
  *H01J 49/26* (2006.01)
  *G16B 15/00* (2019.01)

(52) U.S. Cl.
  CPC ............ *G16C 20/20* (2019.02); *H01J 49/004* (2013.01); *H01J 49/0036* (2013.01); *H01J 49/26* (2013.01)

(56) References Cited

OTHER PUBLICATIONS

Carlsson, G. et al. Topological Data Analysis and Machine Learning Theory, Banff International Research Station (BIRS) for Mathematical Innovation and Discovery, work shop Oct. 15-19, 2012 (Year: 2012).*

Bocker, S. et al. Determination of glycan structure from tandem mass spectra. IEEE/ACM Trans. Comput. Biol. Bioinform. 8, 976-86(2011).

Cooper, C. A. et al. GlycoMod—a software tool for determining glycosylation compositions from mass spectrometric data. Proteomics 1, 340-9 (2001).

Dong, L. et al. An Accurate de novo Algorithm for Glycan Topology Determination from Mass Spectra. IEEE/ACM Trans. Comput. Biol. Bioinform. 12, 568-78 (2015).

Ethier, M. et al. Automated structural assignment of derivatized complex N-linked oligosaccharides from tandem mass spectra. Rapid Commun. Mass Spectrom. 16, 1743-54 (2002).

Ethier, M. et al. Application of the StrOligo algorithm for the automated structure assignment of complex N-linked glycans from glycoproteins using tandem mass spectrometry. Rapid Commun. Mass Spectrom. 17, 2713-20 (2003).

Gaucher, S. P. et al. STAT: a saccharide topology analysis tool used in combination with tandem mass spectrometry. Anal. Chem. 72, 2331-6 (2000).

Hong, P. et al. GlycoDeNovo—an Efficient Algorithm for Accurate de novo Glycan Topology Reconstruction from Tandem Mass Spectra, American Society for Mass Spectrometry, Aug. 7, 2017.

International Searching Authority, International Search Report and Written Opinion for application PCT/US2018/035649, dated Jun. 1, 2018.

Kumozaki, S. et al. A Machine Learning Based Approach to de novo Sequencing of Glycans from Tandem Mass Spectrometry Spectrum. IEEE/ACM Trans. Comput. Biol. Bioinform. 12, 1267-74 (2015).

Lohmann, K. K. et al. GlycoFragment and GlycoSearchMS: web tools to support the interpretation of mass spectra of complex carbohydrates. Nucleic Acids Res. 32, W261-6 (2004).

Shan, B.; et al. Complexities and algorithms for glycan sequencing using tandem mass spectrometry. J. Bioinform. Comput. Biol. 6, 77-91 (2008).

Tang, H. et al. Automated interpretation of MS/MS spectra of oligosaccharides. Bioinformatics 21 Suppl 1, i431-9 (2005).

Tseng, K. et al. Catalog-library approach for the rapid and sensitive structural elucidation of oligosaccharides. Anal. Chem. 71, 3747-54 (1999).

\* cited by examiner

| SHORT NAME | FORMULA | STRUCTURE (CFG WITH LINKAGE PLACEMENT NOTATION) |
|---|---|---|
| SLA | [Neu5Ac(α2-3) Gal(β1-3)][Fuc(α1-4)]GlcNAc | |
| SLX | [Neu5Ac(α2-3) Gal(β1-4)][Fuc(α1-3)]GlcNAc | |
| LEWIS B | [Fuc(α1-2) Gal(β1-3)] [Fuc(α1-4)]GlcNAc | |
| LEWIS Y | [Fuc(α1-2) Gal(β1-4)] [Fuc(α1-3)]GlcNAc | |
| LNT | Gal(β1-3)GlcNAc(β1-3) Gal(β1-4)Glc | |
| LNnT | Gal(β1-4)GlcNAc(β1-3) Gal(β1-4)Glc | |
| LNFP I | Fuc(α1-2) Gal(β1-3)GlcNAc(β1-3) Gal(β1-4)Glc | |
| LNFP II | [Gal(β1-3)] [Fuc(α1-4)]GlcNAc(β1-3)Gal(β1-4)Glc | |
| LNFP III | [Gal(β1-4)] [Fuc(α1-3)]GlcNAc(β1-3)Gal(β1-4)Glc | |
| CelHex | Glc(β1-4) Glc(β1-4) Glc(β1-4) Glc(β1-4) Glc(β1-4) Glc | |
| MalHex | Glc(α1-4)Glc(α1-4) Glc(α1-4) Glc(α1-4) Glc(α1-4) Glc | |

FROM
FIG. 7A

| | | |
|---|---|---|
| N002 | [Neu5Ac(α2-3) Gal(β1-4) GlcNAc(β1-2)Man(α1-3)] [Neu5Ac(α2-3) Gal(β1-4) GlcNAc(β1-2)Man(α1-6)] Man(β1-4) GlcNAc(β1-4) GlcNAc | |
| N003 | [Neu5Ac(α2-6) Gal(β1-4) GlcNAc(β1-2)Man(α1-3)] [Neu5Ac(α2-6) Gal(β1-4) GlcNAc(β1-2)Man(α1-6)] Man(β1-4) GlcNAc(β1-4) GlcNAc | |
| N012 | [Neu5Ac(α2-3) Gal(β1-4) GlcNAc(β1-2)Man(α1-3)] [[Man(α1-3)] [Man(α1-6)] Man(α1-6)] Man(β1-4) GlcNAc(β1-4) GlcNAc | |
| N013 | [Neu5Ac(α2-3) Gal(β1-4) GlcNAc(β1-2)Man(α1-3)] [[Man(α1-3)] [Man(α1-6)] Man(α1-6)] Man(β1-4) GlcNAc(β1-4) GlcNAc | |
| N222 | [Neu5Ac(α2-3) Gal(β1-4) GlcNAc(β1-2)Man(α1-6)] [Gal(β1-4) GlcNAc(β1-2) Man(α1-3)] Man(β1-4) GlcNAc(β1-4) GlcNAc | |
| N223 | [Neu5Ac(α2-6) Gal(β1-4) GlcNAc(β1-2)Man(α1-6)] [Gal(β1-4) GlcNAc(β1-2) Man(α1-3)] Man(β1-4) GlcNAc(β1-4) GlcNAc | |
| N233 | [Neu5Ac(α2-3) Gal(β1-4) GlcNAc(β1-2)Man(α1-3)] [Neu5Ac(α2-6) Gal(β1-4) GlcNAc(β1-2)Man(α1-6)] Man(β1-4) GlcNAc(β1-4) GlcNAc | |
| NA2F | [Gal(β1-4) GlcNAc(β1-2)Man(α1-6)][Gal(β1-4) GlcNAc(β1-2)Man(α1-3)] Man(β1-4) GlcNAc(β1-4) [Fuc(α1-6)] GlcNAc | |
| A2F | [Neu5Ac(α2-6) Gal(β1-4) GlcNAc(β1-2)Man(α1-3)] [Neu5Ac(α2-6) Gal(β1-4) GlcNAc(β1-2)Man(α1-6)] Man(β1-4)GlcNAc(β1-4) [Fuc(α1-6)] GlcNAc | |
| Man9 | [[Man(α1-2) Man(α1-6)][Man(α1-2)Man(α1-3)] Man(α1-6)] [Man(α1-2)] Man(α1-2)Man(α1-3)] Man(β1-4) GlcNAc(β1-4) GlcNAc | |

FIG. 7B

| GLYCAN | REM | METAL | #PEAKS | #INTERPRETABLE | #RECONSTRUCTED | #CANDIDATES | RANK BY SPN | RANK BY IonClassifier |
|---|---|---|---|---|---|---|---|---|
| LEWIS B | O18 | Cs | 177 (70) | 28 | 6 | 3 | 2 (1) | 2 (1) |
| LEWIS B | O18 | Na | 90 (33) | 30 | 7 | 3 | 1 (0) | 1 (0) |
| LEWIS Y | O18 | Cs | 151 (62) | 22 | 7 | 3 | 2 (1) | 2 (1) |
| LEWIS Y | O18 | Na | 147 (52) | 29 | 8 | 3 | 1 (1) | 1 (1) |
| LNFP 1 | O18 | Cs | 99 (38) | 25 | 10 | 12 | 1 (2) | 1 (2) |
| LNFP 1 | O18 | Na | 59 (19) | 18 | 5 | 1 | 1 (0) | 1 (0) |
| LNFP 2 | O18 | Cs | 66 (25) | 22 | 9 | 9 | 1 (2) | 1 (2) |
| LNFP 2 | O18 | Na | 73 (26) | 19 | 9 | 9 | 1 (2) | 1 (2) |
| LNFP 3 | O18 | Cs | 72 (27) | 25 | 10 | 12 | 1 (2) | 1 (2) |
| LNFP 3 | O18 | Na | 57 (19) | 19 | 12 | 16 | 1 (4) | 1 (0) |
| NA2F | O18 | Na | 1745 (783) | 600 | 47 | 1 | 1 (0) | 1 (0) |
| Man9 | O18 | Na | 1944 (905) | 664 | 131 | 18 | 6 (4) | 1 (4) |
| A2F | RED | Na | 1457 (659) | 607 | 211 | 73 | 40 (14) | 1 (1) |
| N002 | D-R | Na | 265 (114) | 35 | 11 | 1 | 1 (0) | 1 (0) |
| N003 | D-R | Na | 163 (70) | 18 | 8 | 1 | 1 (0) | 1 (0) |
| N012 | D-R | Na | 409 (182) | 62 | 16 | 11 | 1 (0) | 1 (0) |
| N013 | D-R | Na | 362 (160) | 40 | 15 | 5 | 1 (0) | 1 (0) |
| N222 | D-R | Na | 377 (163) | 147 | 24 | 9 | 1 (0) | 1 (0) |
| N223 | D-R | Na | 490 (219) | 58 | 17 | 6 | 1 (0) | 1 (1) |
| N233 | D-R | Na | 292 (127) | 37 | 8 | 1 | 1 (0) | 1 (0) |
| LEWIS B | NONE | Na | 125 (48) | 34 | 8 | 3 | 1 (1) | 1 (0) |
| LNT | NONE | Na | 319 (134) | 23 | 7 | 5 | 1 (0) | 1 (0) |
| LNnT | NONE | Na | 279 (114) | 23 | 9 | 5 | 1 (1) | 1 (1) |
| SLA | NONE | Na | 230 (84) | 64 | 18 | 22 | 1 (2) | 1 (2) |
| SLX | NONE | Na | 351 (143) | 60 | 18 | 22 | 1 (2) | 1 (2) |
| CelHex | NONE | Na | 491 (173) | 61 | 11s | 11 | 1 (0) | 1 (0) |
| MalHex | NONE | Na | 450 (201) | 39 | 11 | 11 | 1 (0) | 1 (0) |

FIG. 8

SYSTEM AND METHOD FOR DETERMINING GLYCAN TOPOLOGY USING TANDEM MASS SPECTRA

CROSS-REFERENCE TO RELATED APPLICATIONS

This application represents the U.S. National Stage of International Application No. PCT/US2018/035649, filed Jun. 1, 2018, which claims priority to U.S. Provisional Patent Application Ser. No. 62/513,495, filed Jun. 1, 2017, and U.S. Provisional Patent Application Ser. No. 62/531,229, filed Jul. 11, 2017; the entire contents of which are herein incorporated by reference.

STATEMENT REGARDING FEDERALLY SPONSORED RESEARCH

This invention was made with government support under grant number P41 GM104603, awarded by the National Institutes of Health (Mass Spectrometry Resource for Biology and Medicine) and under grant number U01 CA221234, awarded by the National Institutes of Health (an open-source software suite for processing glycomics and glycoproteomics mass spectral data). The government has certain rights in the invention.

BACKGROUND

Glycosylation is a common modification by which a glycan (or oligosaccharide) is covalently attached to a target biomolecule such as proteins and lipids. It serves important purposes in many biological processes, including protein folding and clearance, cell adhesion, and immunological responses, among others. Glycosylation is one of the key factors that determine the solubility, stability and efficacy of many biopharmaceuticals. Change in glycosylation pattern is often observed under different disease conditions, such as tumorigenesis. Glycan structural analysis is essential for understanding their diverse roles in biological systems, yet it remains a challenging task, in part due to the vast number of topologies that they may assume even for a moderate-sized glycan. Glycans are tree ensembles of monosaccharides linked via glycosidic bonds. A glycosidic bond is formed via condensation reaction between the hemiacetal group of one monosaccharide (the non-reducing end residue) and a hydroxyl group of another (the reducing end residue). Theoretically, there could be up to four branches at any branching point in an oligosaccharide though these seldom occur naturally because of steric hindrance.

A major challenge in glycomics is the characterization of complex glycan structures that are essential for understanding the diverse roles of glycans in many biological processes. Recently, there has been a boom in -omics that has been catalyzed by the application of tandem mass spectrometry (MS/MS) methods to biopolymer sequencing. However, compared to the rapid growth of proteomics, progress in glycomics has been modest. This is, in part due to the structural complexity of glycans and the necessity to determine branching patterns, linkages, and stereochemical configurations of the glycans in order to fully define the glycan's structure. The simultaneous presence of many isomeric glycans in biological samples adds another layer of challenge to structural glycomics, demanding analytical tools that can provide structural details and work well in tandem with various glycan separation methods, such as liquid chromatography (LC), capillary electrophoresis, and ion mobility spectrometry (IMS), for analysis of complex glycan mixtures.

Several tools exist for determining the topologies of glycans. For example, one technique is known as a catalog-library approach, where experimental spectra are searched against pre-built glycan databases. The accuracy of the search results depends not only on the quality of the query (e.g., the tandem MS data) but also on the quality and completeness of the databases. To date, glycan databases are often populated with lower-quality spectral data obtained on ion trap and time-of-flight instruments, typically generated by collision-induced dissociation (CID). This can adversely affect the performance of database searching algorithms that identify and score candidate structures based on the similarity of the query to spectra in the database, especially for experimental data generated by radical-induced fragmentation methods, and/or on higher-performance MS instruments. Another example includes brute-force search methods that may be used to exhaustively compare an experimental tandem mass spectrum to those of all possible theoretical structures. However, the number of possible structures increases exponentially as the number of monosaccharides in a glycan increases, and the search spaces quickly becomes too big to explore for large glycans.

Currently, there is a need for a reconstruction technique that can accurately characterize the structure of both large macromolecules and small molecules with reduced computational complexity, and through the use of a method that does not rely on a database of known structures.

SUMMARY

The present disclosure overcomes the aforementioned drawbacks by providing a de novo computational approach that builds an accurate elucidation of molecular topologies that are produced from mass spectroscopy data.

In some aspects, the present disclosure provides a method of determining molecular structure using a mass spectrometer. The method includes acquiring a mass spectrum of a macromolecule that includes mass spectrum peaks comprising a precursor ion and fragment ions, where the precursor ion has a first mass-to-charge ratio. The method includes identifying one or more of the fragment ions to produce a candidate set comprising monomer subunit ions that are combinable with one or more inferable constituent. The candidate set including at least one candidate having the first mass-to-charge ratio within a selected mass tolerance. Reconstructing a topology for the precursor ion that is within the mass tolerance.

In one aspect, the present disclosure provides a method for determining a topology of a molecule using a mass spectrometer. The method includes acquiring a mass spectrum of a molecule that includes mass spectrum peaks corresponding to a precursor ion and fragment ions. At least a portion of the fragment ions in the mass spectrum are then identified as corresponding to one or more monomer subunit ion of the precursor ion. Identifying the fragment ions as one or more monomer subunit ion may be performed by appending one or more of the fragment ions to an inferable constituent to produce a candidate topology building block, and storing the candidate topology building block in a candidate pool as corresponding to one or more of the monomer subunit ion if the combined mass of the inferable constituent and one or more of the fragment ions satisfy a first user-defined mass tolerance. One or more candidate topology of the precursor ion may then be produced by combining a plurality of the topology building blocks that satisfy a second user-defined mass tolerance for the precursor ion. The method may also include selecting a topology for the precursor ion by ranking the one or more candidate topology based on a candidate topology score, and selecting the candidate topology with the highest candidate topology score.

In another aspect, the present disclosure provides a mass spectrometry unit that comprises an inlet port configured to receive a sample that includes a macromolecule comprising monomer subunits, and an ion source configured to ionize the sample to produce a precursor ion, the precursor ion having a first mass-to-charge ratio. The mass spectrometry unit also includes a mass analyzer configured to dissociate a portion of the precursor ion to produce fragment ions, where the mass analyzer configured to separate a fraction of the precursor ion and the fragment ions. A detector may also be configured to produce detection signals corresponding to the fraction of the precursor ion and the fragment ions. The mass spectrometry unit may further include a controller configured to receive the detection signals, the controller programmed to: acquire a mass spectrum of a molecule, the mass spectrum including mass spectrum peaks corresponding to a precursor ion and fragment ions, wherein the precursor ion corresponds to an ionized product of the molecule and the fragment ions correspond to dissociated products of the molecule; identify at least a portion of the fragment ions in the mass spectrum as corresponding to one or more monomer subunit ion of the precursor ion, wherein the one or more monomer subunit ion is identified by appending one or more of the fragment ions to an inferable constituent to produce a topology building block, and storing the topology building block in a candidate pool as corresponding to one or more of the monomer subunit ion if the combined mass of the inferable constituent and one or more of the fragment ions satisfy a first user-defined mass tolerance; and c) reconstruct one or more candidate topology of the precursor ion by combining a plurality of the topology building blocks that satisfy a second user-defined mass tolerance for the precursor ion.

In another aspect, a method for determining a topology for a molecular using a computer system is provided. The method includes providing an acquired mass spectrum of a molecule to a computer system, where the mass spectrum includes mass spectrum peaks corresponding to a precursor ion and fragment ions. The computer system is then programmed to identify at least a portion of the fragment ions in the mass spectrum as corresponding to one or more monomer subunit ion of the precursor ion, wherein the one or more monomer subunit ion is identified by appending one or more of the fragment ions to an inferable constituent to produce a topology building block, and storing the topology building block in a candidate pool as corresponding to one or more of the monomer subunit ion if the combined mass of the inferable constituent and one or more of the fragment ions satisfy a first user-defined mass tolerance. The computer system is then programmed to reconstruct one or more candidate topology of the precursor ion by combining a plurality of the topology building blocks that satisfy a second user-defined mass tolerance for the precursor ion.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 7 is a table providing an example set of glycans tested using the methods in accordance with the present disclosure.

FIG. 8 is a table providing non-limiting test results for reducing-end modified glycans that are produced using methods in accordance with the present disclosure.

DETAILED DESCRIPTION

Described herein are methods for determining a topology, or molecular formula, of a molecule using experimental mass spectroscopy data.

Suitable molecules for use with the systems and methods presented herein may include macromolecules and small molecules. As used herein, a macromolecule may comprise any repeatable unit (e.g., monomer subunit) or pairs of units that may be coupled together to produce the macromolecule. Exemplary molecules of the present disclosure may include natural and synthetic macromolecules. Non-limiting examples of natural macromolecules include, but are not limited to carbohydrates or glycans (e.g., composed of monosaccharides), nucleic acids (e.g., composed of nucleotides), proteins and/or peptides (e.g., composed of amino acids), lipids (e.g., composed of fatty acids), derivatives and mixtures thereof. Suitable synthetic macromolecules may include one or more monomer subunit selected from ethylene, propylene, styrene, tetrafluoroethylene, vinyl chloride, derivatives and mixtures thereof.

Figure 1A:
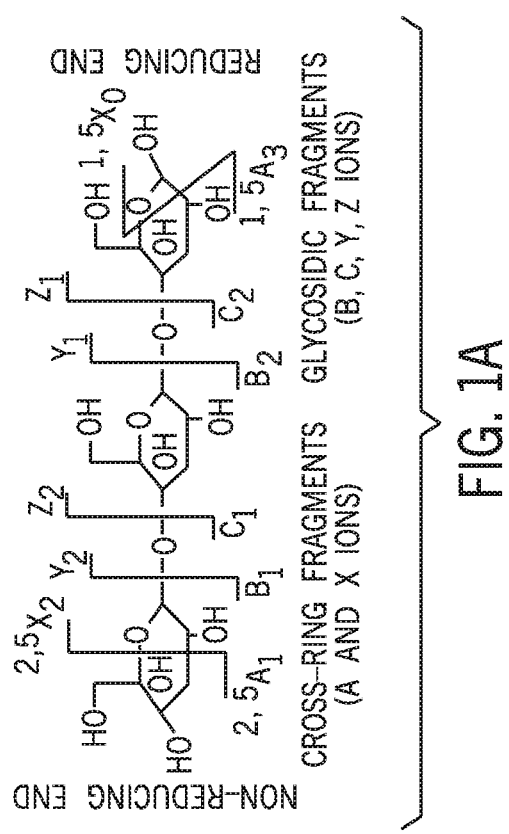
FIG. 1A is an illustration of a glycan fragmentation nomenclature system for use in accordance with the present disclosure.
Figure 1B:
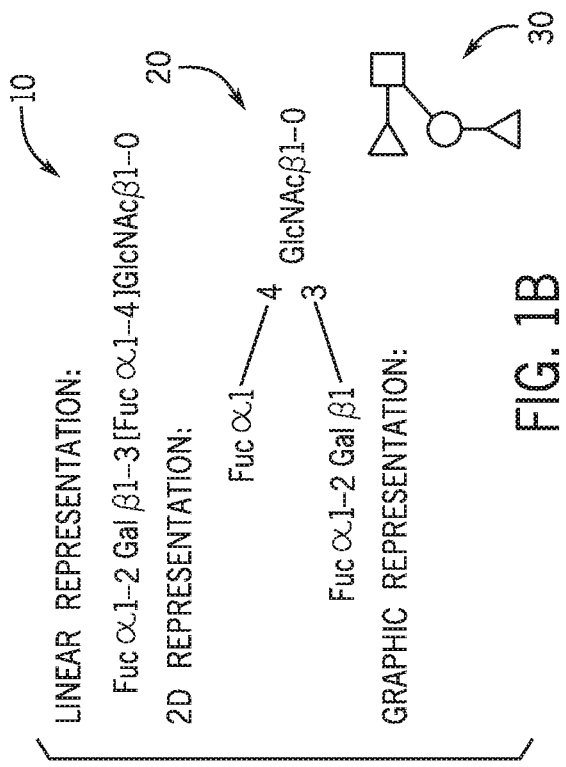
FIG. 1B is a linear representation, a two-dimensional representation, and a graphic representation of a glycan structure for use in accordance with the present disclosure.

Owing to the structure complexity of glycans, the technology for determining glycan structure from experimental data has lagged behind those for other classes of biological macromolecules. In one embodiment, the methods described herein can accurately and efficiently determine the topology, or molecular formula, for glycans using experimental data. Referring to FIG. 1A-B, a non-limiting example of a glycan is provided to illustrate dissociation patterns of glycans during mass spectroscopy experiments. As shown in FIG. 1A, a single glycosidic cleavage during a mass spectroscopy experiment produces monomer subunit ions, such as B, C, Y, and Z ions, whereas cross-ring cleavages generate fragment ions, such as, A and X ions. Internal fragment ions, or fragment ions with loss of multiple branches may also be formed by two or more glycosidic and/or cross-ring cleavages. In some aspects, the methods presented herein group fragment ions, such as A and X ions, and internal fragment ions into a category termed O ions (i.e., Other ions). The monomer subunit glycosidic fragments are important for topology deduction. Since a Y ion differs in mass from its related Z ion by that of a water molecule, as does a B ion from its related C ion, C and Z ions provide redundant information to B and Y ions. A and X ions are useful for deciphering the branching pattern and linkages, as well as for ranking the candidate topologies. The topology of a glycan can be represented as a tree with nodes representing monosaccharide residues and edges representing glycosidic linkages. For example, FIG. 1B provides an illustration of a linear representation 10 of a glycan, a two-dimensional representation 20 of a glycan, and a graphic representation of a glycan 30.

Figure 2:
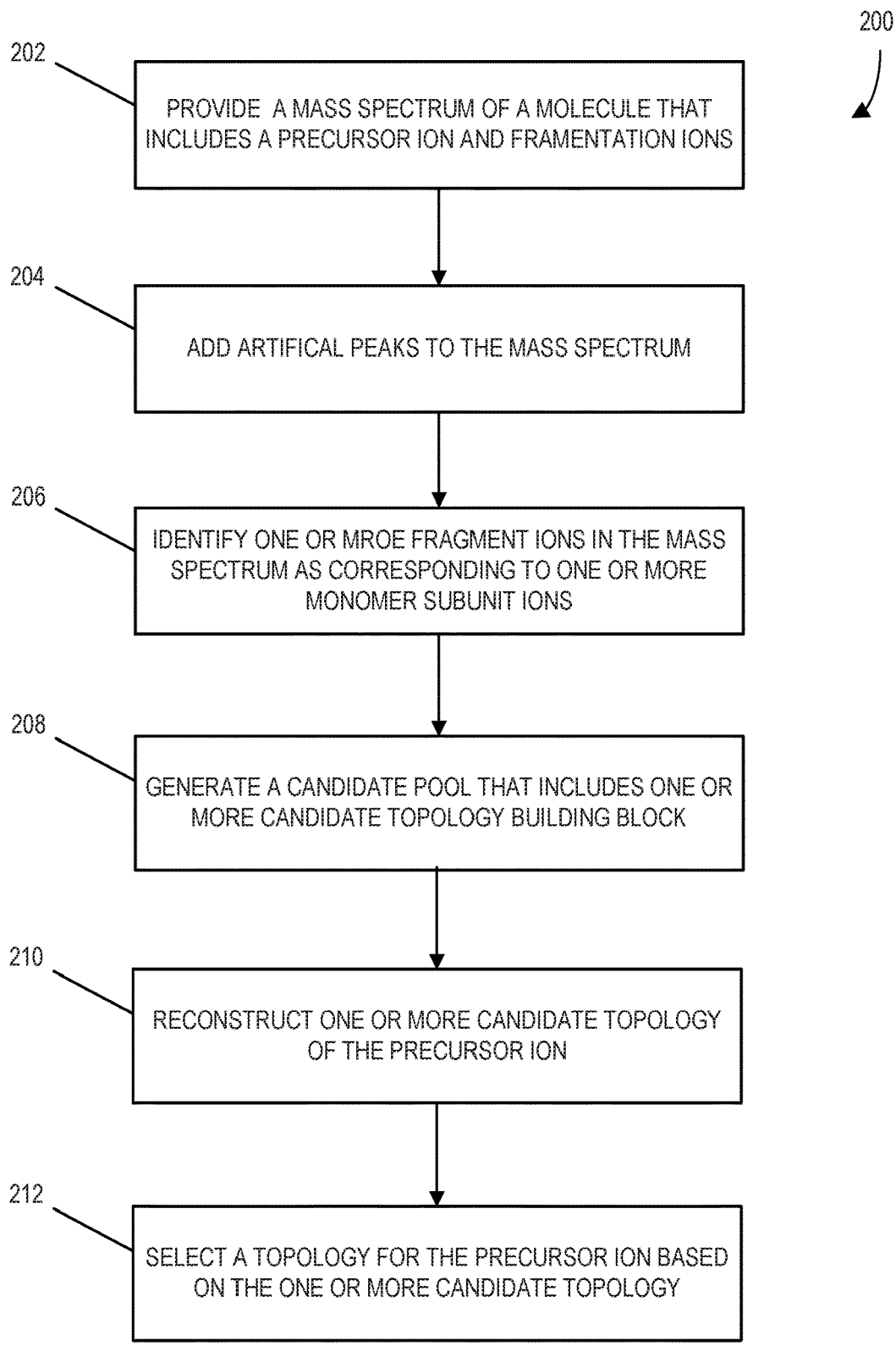
FIG. 2 is a graphical illustration of an example method for determining a topology of a molecule in accordance with one aspect of the present disclosure.

Referring to FIG. 2, a flowchart is provided as setting forth the steps of an example method 200 for determining a topology for a molecule using a computer system. The method 200 may also be referred to throughout the disclosure as "GlycoDeNovo." The method includes providing a mass spectrum to a computer system that includes mass spectrum peaks corresponding to a precursor ion and fragment ions, as indicated at step 202. In some aspects, the precursor ion corresponds to an ionized product of the molecule and the fragment ions correspond to dissociated products of the molecule. The mass spectrum can be provided to the computer system by retrieving previously acquired data from a memory or other data storage device. In some aspects, the mass spectrum can also be provided to the computer system by acquiring the data using a mass spectrometry unit and communicating the acquired data to the computer system, which may form a part of the mass spectrometry unit.

In some aspects, the method 200 includes computationally adding artificial mass spectrum peaks to the mass spectrum to compensate for a portion of the fragmentation ions that are unobservable in the experimental spectrum, as indicated at step 204. Adding artificial mass spectrum peaks to the mass spectrum may facilitate the reconstruction of the experimental data to generate a topology for the molecule because although each monomer subunit ion (e.g., glycosidic cleavage) could in theory generate a pair of complementary ions, not all fragments are observed in the experimental data due to the lack of charge carrier, secondary fragmentation, or other reasons. In some aspects, peaks complementary to a non-reducing-end of glycosidic fragments are added to the mass spectrum to facilitate reconstruction.

In some aspects, the method also includes identifying at least a portion of the fragment ions in the mass spectrum as corresponding to one or more monomer subunit ion of the precursor ion, as indicated in step 206. Identifying the fragment ions as monomer subunit ions may include appending one or more of the fragment ions to an inferable constituent to produce a candidate topology building block. As indicated in step 208, the candidate topology building block may then be stored in a candidate pool as corresponding to one or more of the monomer subunit ions if the combined mass (or mass-to-charge ratio) of the inferable constituent and the one or more fragment ions satisfies a user-defined mass tolerance. For example, satisfying the user-defined mass tolerance may be achieved if the combined mass-to-charge ratio of the inferable constituent and the one or more fragment ion falls within a specified range around a predicated combined mass of the inferable constituent and the one or more fragment ion. In one non-limiting example, the user-defined mass tolerance may be 0.02 Da or less (or the m/z equivalent). In other aspects, the user-defined mass tolerance may be 0.005 Da or less (or the m/z equivalent). In some aspects, the user-defined mass tolerance ranges between 0.005 and 0.02 Da (or the m/z equivalent).

In some aspects, the candidate topology building block is produced by first identifying lighter fragment ions in the mass spectrum as corresponding to one or more monomer subunit ion, and proceeds by searching for some or all allowable combinations of fragment ions in the candidate pool that can be appended to a inferable constituent to obtain the candidate topology building block with a mass within the first user-defined mass tolerance. In one non-limiting example, steps 206-208 may include identifying fragment peaks as corresponding to B or C glycosidic ions (e.g., monomer subunit ions) of a glycan ion (e.g., precursor ion) by using interpretations of preceding peaks. In each iteration, the method 200 interprets some or all of the fragment ion peaks as corresponding to B or C glycosidic ions by attaching up to four branches to a monosaccharide (e.g., inferable constituent), wherein the branches are interpretations of fragment ion peaks that are lighter than the one being interpreted. In some aspects, the monomer subunit ions correspond to a non-reducing end of a glycosidic fragment. The candidate topology building blocks may be represented in graphical form. For example, in some aspects, steps 206-208 include generating an interpretation-graph that includes nodes and edges to respectively represent fragment peaks and how a fragment peak can be interpreted as a monomer subunit ion by using interpretations of preceding peaks. A non-limiting example of an interpretation-graph is provided in FIG. 5.

In some aspects, the method 200 includes reconstructing one or more candidate topology of the precursor ion by combining multiple candidate topology building blocks to satisfy a second user-defined mass tolerance for the precursor ion, as indicated in step 210. In some aspects, the method 200 includes reconstructing all the possible candidate topologies for the precursor ion. In one non-limiting example, the user-defined mass tolerance may be 0.02 Da or less (or the m/z equivalent). In other aspects, the user-defined mass tolerance may be 0.005 Da or less (or the m/z equivalent). In some aspects, the user-defined mass tolerance ranges between 0.005 and 0.02 Da (or the m/z equivalent).

The method may also include selecting a topology for the precursor ion by ranking the one or more candidate topology based on a candidate topology score, and selecting the candidate topology having the highest candidate topology score, as indicated by step 212. In some aspects, selecting the topology for the precursor ion includes applying a machine-learning technique to generate a candidate topology score. The candidate topology score may be based on the likelihood that the fragment ions in the mass spectrum correspond to the one or more monomer subunit ion identified in the candidate pool. The candidate with the highest candidate topology may then be selected as the topology for the precursor ion. In one non-limiting example, the candidate topology score may include defining a mass difference window in the mass spectrum that includes one or more of the fragment ions in the mass spectrum, and expressing the fragment ions as an array of contextual features to determine if the fragment ions in the mass difference window correspond to a monomer subunit ion. A positive value may then be assigned to mass spectrum peaks that contain the highest likelihood of corresponding to a monomer subunit ion based on the array of contextual features, and a negative value may be assigned to mass spectrum peaks that contain the lowest likelihood of corresponding to a monomer subunit ion based on the array of contextual features.

In one non-limiting example, steps 206-208 may be performed using an algorithm dubbed, "PeakInterpreter," and steps 210-212 may be performed using an algorithm dubbed "CandidateSetReconstructor." In some aspects, PeakInterpreter builds an interpretation-graph that specifies how to interpret each peak using the topologies of other peaks with lighter masses. In some aspects, CandidateSetReconstructor takes the interpretation-graph and reconstructs all candidate topologies of the precursor ion that satisfy the user-defined mass accuracy constraint. The algorithms are provided in detail below, along with symbols and data structures used. However, these algorithms are provided for illustration only, and are not intended to limit the disclosure.

In some aspects, G may represent a data set comprising monomer subunits classes of interest. In some forms an enriched peak list is created that includes computationaly added artificial peaks. The enriched peak list may comprise a set of peaks sorted ascendingly by their masses $\{m_1, m_2, \ldots, m_N\}$, where $m_N$ is the observed mass of the precursor ion. The user-defined mass accuracy or tolerance may be defined by $\tau$. Each peak, say the n-th peak, may have a candidate set $s_n$, which is represented as <peakID, cmass, lmass, hmass, topoReconstructionSet, topologySet>, where peakID=n, cmass=$m_n$, mass and hmass respectively are the low- and high-mass bounds of the topologies that can be used to interpret this peak and are stored in topologySet, and topoReconstructionSet may be a set containing information for deriving topologySet. Each member in $s_n$.topoReconstructionSet is an object topoReconstruction=<root, branchSet, topologySet> representing a set of topologies that use the same root or inferable constituent (e.g., a monosaccharide class ∈ G) and choose their branches from branchSet (each member in branchSet contributes one branch). Each member in branchSet may be a candidate set of a peak preceding the n-th peak. In some aspects, each topology in topoReconstruction.topologySet chooses one branch from the topologySet of each member in topoReconstruction.branchSet.

The topology may be represented by a structure <mass, representation, supports>, where mass is its theoretical mass, representation is a text string following the modified IUPAC condensed text nomenclature without linkage information, and supports contains peaks in the enriched peak list that can be interpreted as B- or C-type ions and be generated from this topology. In some aspects, S may be used to represent the candidate pool comprising all non-empty candidate sets.

In one non-limiting example, PeakInterpreter may be represented by:

Algorithm I: S = Peak Interpreter($\{m_1, m_2, \ldots, m_N\}$)

(1) Initialize the candidate pool S = {∅}.
(2) for n = 1 to N
(3)  Initialize the candidate set $s_n$ of the n-th peak: $s_n$.cmass = $m_n$, $s_n$.lmass = mn − $\tau$, $s_n$.hmass = $m_n$ + $\tau$, $s_n$.topoReconstructionSet = ∅, $s_n$.topologySet = ∅.
(4)  for all possible combinations of up to 4 possible sets $s_a, s_b, s_c, s_d \in$ S
(5)   Calculate lm = $s_a$.lmass + $s_b$.lmass + $s_c$.lmass + $s_d$.lmass
       hm = $s_a$.hmass + $s_b$.hmass + $s_c$.hmass + $s_d$.hmass
       δ = mass difference caused by creating a B-ion (or the precursor ion if n = N) by linking $s_a, s_b, s_c, s_d$ to a monosaccharide.
(6)   if ∃ g ∈ G s.t. (lm, hm) = ($m_n$ − $\tau$, $m_n$ + $\tau$) ∩ (g.mass + lm + δ, g.mass + hm + δ) ≠ ∅
(7)    Create a topoReconstruction object r = <g, {$s_a, s_b, s_c, s_d$}, ∅>, and add r to $s_n$.topoReconstructionSet.
       Set $s_n$.lmass = min($s_n$.lmass, lm) and $s_n$.hmass = max($s_n$.hmass, hm).
(8)   end
(9)  end
(11)  if $s_n$.topoReconstructionSet ≠ ∅, add $s_n$ to S, end
(12) end As illustrated above, PeakInterpreter may allow candidate topologies to have up to 4 branches at each branching point. In some aspects, this constraint may be lowered to increase computation speed, or it may be increased for some monomer subunit ions. PeakInterpreter maintains a candidate pool where each candidate topology building block serves as a potential building block for interpreting a heavier peak. PeakInterpreter starts from the lightest peak and tries to interpret some or all of the mass spectrum peaks as a monomer subunit ion (e.g., B ion and C ion) or the precursor ion by searching for all allowable combinations of fragment ions in the candidate pool S (steps 4-9) that can be appended to a root or inferable constituent (e.g., monosaccharide) g to obtain a candidate set or pool with a mass within the accuracy range specified by $\tau$. In some aspects, the mass difference δ in step 5 depends on the ion type and macromolecule derivation method deployed, (i.e., permethylation). The intensities of the non-precursor peaks may be interpretable by PeakInterpreter to normalize the intensities of all peaks into z-scores.

Topologies may be reconstructed at $s_n$.topologySet, however reconstruction can be delayed to a later step. In some aspects, topology reconstruction can be done in CandidateSetReconstructor after PeakInterpreter terminates. PeakInterpreter may not have the accurate mass of each candidate topology, which is yet to be reconstructed, the test performed at step 6 gives an estimate of the mass range tight enough to include all true positives, but it may also include a small number of false positives (i.e., topologies with masses outside of the accuracy range). Because each interpreted peak is still represented as one yet-to-be-reconstructed candidate set, the false positives will not increase the computational complexity, and they will be removed later by CandidateSetReconstructor.

In the case for glycans, the complexity of building an interpretation-graph is $O(|G| \times N^{H+1})$, where G is the monosaccharide set, N is the number of peaks in the given spectrum, and H≤4 is the maximal branching number permitted. The computation of PeakInterpreter mainly resides in the for-loop between steps 4-9 whose complexity is $O(|G| \times |S^{(n)}|^H)$, where $S^{(n)}$ is the value of the candidate pool S at the n-th loop and $|S^{(n)}|$ is the size of $S^{(n)}$ (i.e., the number of interpretable peaks up to the n-th loop). The overall complexity of PeakInterpreter is $O(|G| \times \Sigma_{n=1}^{N} |S^{(n)}|^H)$. Since $|S^{(n)}| \leq n$, $O(|G| \times \Sigma_{n=1}^{N} |S^{(n)}|^H) = O(|G| \times \Sigma_{n=1}^{N} = n^H) = O(|G| \times N^{H+1})$.

After obtaining the interpretation-graph, the candidate set object of the precursor ion into CandidateSetReconstructor to reconstruct legal (e.g., fall within a user-defined mass tolerance) candidate topologies. CandidateSetReconstructor first checks if each topoReconstruction object r in the input candidate set s has been reconstructed. If not, it recursively calls itself to reconstruct some or all branches of r. Then CandidateSetReconstructor creates legal topologies of r (steps 11-19), which are rooted at r.root and satisfy the mass accuracy constraint. At step 14, the branches are linked by their alphabetic order to r.root so that isomorphic topologies can be effectively detected and removed at step 16. The union operation at step 15 effectively and efficiently solves the problem of repeated counting of supporting peaks, which has been shown to be a long felt, but unresolved need in the art. Finally, at step 19, the candidate topology set of r is added to that of s. CandidateSetReconstructor runs extremely fast, and its running time is negligible comparing to that of PeakInterpreter.

In one non-limiting example, CandidateSetReconstuctor may be represented by:

fragments; and (2) Y and Z ions provide redundant mass information to B and C ions, and even in cases where only Y and/or Z ions are observed at a cleavage site, their information is recaptured in the enriched peak list. Growing topologies from the reducing end may run into difficulties when dealing with branching points where each of the branches contain more than one monosaccharide residue. In such a scenario, some of the reconstructed topologies can correspond to internal fragments, which are more likely to be missing in data, thus making it difficult to evaluate those topologies.

In some aspects, the present disclosure addresses the issue of missing peaks by considering pairs of monomer subunit ions when interpreting the peaks and during reconstruction. For example, Peakinterpreter may consider monosaccharide pairs rather than individual monosaccharides at step 6 and CandidateSetReconstructor at step 14 may create topologies that either use a monosaccharide pair as the root or use one monosaccharide in the pair as the root and merge the other with one of the branches. Put another way, for each possible ordered pair of monosaccharides [g1, g2] satisfying the mass accuracy constrain, the interpretation graph can be expanded by (1) creating a topoReconstruction object r1 that links sa, sb, sc, and sd to g2 and then another topoReconstruction object r2 that link r1 to g1 or (2) for each s in {sa, sb, sc, sd}, creating a topoReconstruction object r1 that links s to g2 and then another topoReconstruction object r2 that links r1 U ({sa, sb, sc, sd}-s) to g. In some aspects, allowing missing peaks increases the search space, but using this optionally

---

Algorithm II: CandidateSetReconstructor(s)

(1)  if s.topologySet ≠ Ø
(2)     return // s has been reconstructed.
(3)  end
(4)  for each r ∈ s.topoReconstructionSet
(5)     if r.topologySet ≠ Ø
(6)        continue // r has been reconstructed
(7)     end
(8)     for each branch ∈ r.branchSet
(9)        CandidateSetReconstructor( branch )
(10)    end
(11)    for each of all possible branch combinations (a combination is formed by choosing one
           topology from the topologySet of each s ∈ r.branchSet)
(12)       Calculate tmass = total mass of the topology with the chosen branches linked to r.root.
(13)       if tmass ∈ (massLow, massHigh)
(14)          Create a topology t by linking the chosen branches to r.root, let t.mass = tmass.
(15)          t.supports = {peakID} U {peak supports of t's branches}.
(16)          Add t to r.topologySet.
(17)       end
(18)    end
(19)    Add r.topologySet to s.topologySet.
(20) end

---

Unlike previous methods, the present disclosure may use a user-defined mass tolerance (or specified mass range) to confine the search space within the experimental mass accuracy window without reconstructing any topology during the peak interpretation process. The present disclosure may delay topology reconstruction until it finishes deriving the interpretation group of the precursor ion, and hence it may only need to reconstruct topologies that are required to interpret the precursor ion. Since most partial topologies do not lead to precursor ions, this simple strategy dramatically saves the computational time and space. In some aspects, the present disclosure may start from a non-reducing end of a monosaccharide to incrementally build up interpretations of B and C ions because (1) glycosidic fragments are in general substantially more likely to be observed than cross-ring may assist in finding a topology when there are missing cleavages. Biosynthetic rules (e.g., the chitobiose N-glycan core) can also be incorporated to constrain the search space of PeakInterpreter.

Mass spectrometry data can be noisy. In addition, the presence of internal fragments can greatly complicate the de novo topology reconstruction process. These attributes may cause PeakInterpreter to misinterpret some fragment ions. In one non-limiting example, PeakInterpreter may interpret Y, Z, or O ions as B or C ions and generate ambiguities. Misinterpretation may lead to false topologies being ranked as good as or better than the correct topology based on the supporting peak count alone. To address this problem, the present disclosure may apply machine learning technique, dubbed IonClassifier, to distinguish different types of fragment ions. For example, IonClassifier may distinguish B and C ions from other ion types. In some aspects, IonClassifier takes a peak and its context, currently defined as the neighboring peaks within a predetermined mass-difference window (e.g., 105 Da), and classifies the peak as +1 (i.e., a B- or C-ion) or −1 (i.e., a non-B or C ion). The neighboring peaks can be expressed as an array of contextual features (e.g., mass shifts) from the peak of interest. The final score of a candidate topology is calculated by summing up the IonClassifier values of its supporting peaks.

In some aspects, IonClassifier may be trained by boosting the decision tree classifier on experimental tandem mass spectra of a set of known macromolecules. For each macromolecule standard, a computer system or mass spectrometry unit can match its theoretical spectrum to the experimental spectrum to collect the observed context of each theoretical peak found in the experimental spectrum. In one non-limiting example, the computer system or mass spectrometry unit can then group the supporting peaks of candidates into true B ions, true C ions, true Y ions, true Z ions, and O ions, and trained IonClassifier to distinguish true B-ions and true C ions from Y, Z, and O ions. If a supporting peak is interpreted by PeakInterpreter as a B ion, it will be validated by the B-ion classifier of IonClassifier. Similarly, if a supporting peak is interpreted by PeakInterpreter as a C ion, it will be validated by the C-ion classifier of IonClassifier.

Figure 3:
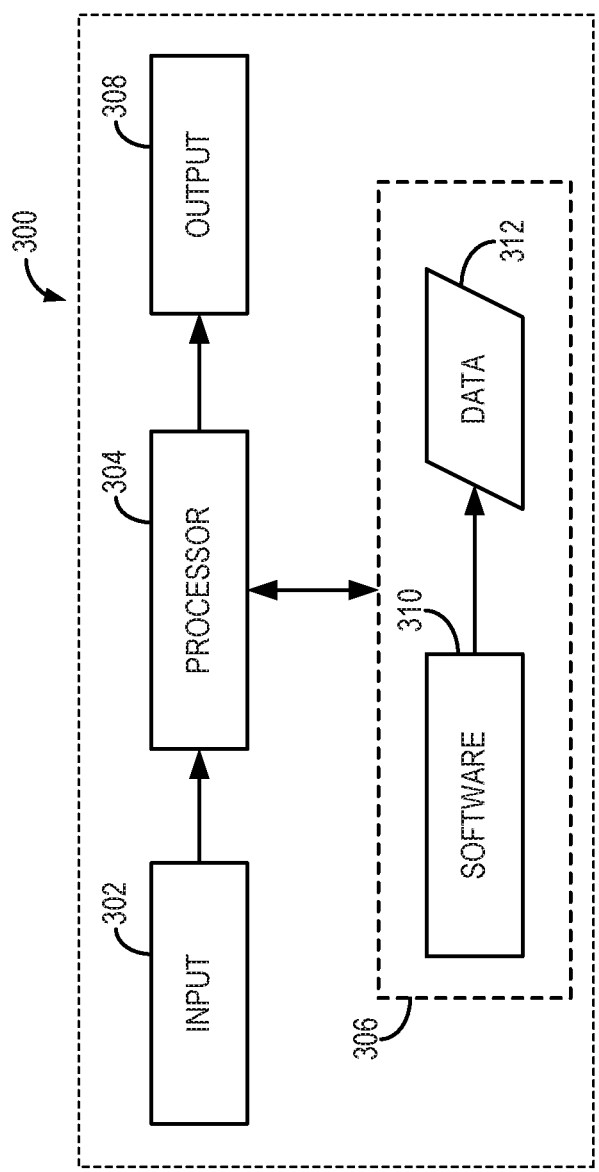
FIG. 3 is a block diagram illustrating an example of a computer system that can implement some aspects of the present disclosure.

Referring now to FIG. 3, a block diagram of an example of a computer system 300 that can be used to implement the methods described herein and, specifically, determine a topology for a molecule using mass spectrometry data. The computer system 300 generally includes an input 302, at least one hardware processor 304, a memory 306, and an output 308. Thus, the computer system 300 is generally implemented with a hardware processor 304 and a memory 306. In some embodiments, the computer system 300 can be implemented, in some examples, by a workstation, a notebook computer, a tablet device, a mobile device, a multimedia device, a network server, a mainframe, one or more controllers, one or more microcontrollers, or any other general-purpose or application-specific computing device.

The computer system 300 may operate autonomously or semi-autonomously, or may read executable software instructions from the memory 306 or a computer-readable medium (e.g., a hard drive, a CD-ROM, flash memory), or may receive instructions via the input 302 from a user, or any another source logically connected to a computer or device, such as another networked computer, server. The input 302 may take any shape or form, as desired, for operation of the computer system 300, including the ability for selecting, entering, or otherwise specifying parameters consistent with operating the computer system 300.

In general, the computer system 300 is programmed or otherwise configured to implement the methods and algorithms in the present disclosure, such as those described with reference to FIG. 2. For instance, the computer system 300 can be programmed to generate a topology for a molecule based on experimental mass spectroscopy data. In some aspects, the computer system 300 may be programmed to access acquired data from a mass spectrometry unit, such as mass spectroscopy data that includes mass spectrum peaks corresponding to a precursor ion and fragment ions. Alternatively, the mass spectrum may be provided to the computer system 300 by acquiring the data using a mass spectrometry unit and communicating the acquired data to the computer system 300, which may be part of the mass spectrometry unit.

The computer system 300 may be further programmed to process the mass spectrum to generate a topology for the molecule of interest. The computer system 300 may identify at least a portion of the fragment ions in the mass spectrum as corresponding to one or more monomer subunit ion of the precursor ion, and the one or more identified monomer subunit ion may be used to generate a candidate pool containing one or more candidate topology building block. From the one or more candidate topology building block, the computer system 300 may reconstruct a candidate topology of the precursor ion that satisfy a user-defined mass tolerance for the precursor ion.

The input 302 may take any suitable shape or form, as desired, for operation of the computer system 300, including the ability for selecting, entering, or otherwise specifying parameters consistent with performing tasks, processing data, or operating the computer system 300. In some aspects, the input 302 may be configured to receive data, such as data acquired with a mass spectrometry unit, such as the system described in FIG. 4. Such data may be processed as described above to generate a topology for the molecule of interest. In addition, the input 302 may also be configured to receive any other data or information considered useful for determining the topology of the molecule using the methods described above.

Among the processing tasks for operating the computer system 300, the one or more hardware processors 304 may also be configured to carry out a number of post-processing steps on data received by way of the input 302. For example, the processor 304 may be configured to generate a topology for the molecule using experimental mass spectrometry data. The processor 304 may be configured to implement the same or similar method tasks as described in FIG. 2.

The memory 306 may contain software 310 and data 312, such as data acquire with a mass spectrometry unit, and may be configured for storage and retrieval of processed information, instructions, and data to be processed by the one or more hardware processors 304. In some aspects, the software may contain instructions directed to processing the input mass spectrum or mass spectroscopy data to be processed by the one or more hardware processors 304. In some aspects, the software 310 may contain instructions directed to processing the mass spectroscopy data or mass spectrum in order to generate a topology of the molecule, as described in FIG. 2. The software may also contain instructions directed to generating a linear representation, a 2D representation, or graphical representation of the topology of the molecule. In some aspects, the software may also contain instructions directed to generating the interpretation-graph, as described in FIG. 2.

Figure 4:
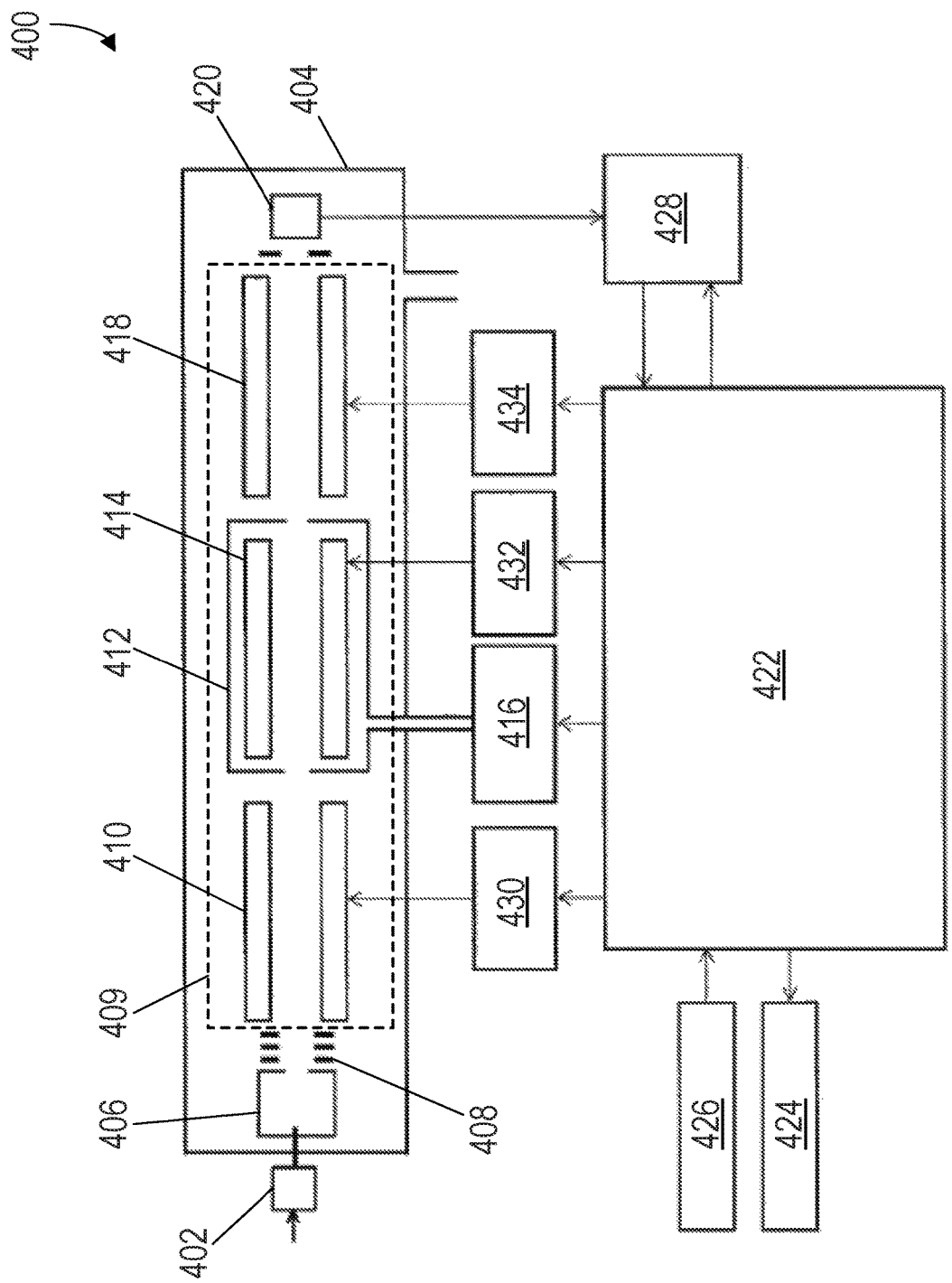
FIG. 4 is a block diagram of a mass spectrometry unit that can implement some aspects of the present disclosure.

Referring to now to FIG. 4, an example of a mass spectrometry unit 400 that can implement the methods described here is illustrated. In general, the mass spectrometry unit 400 includes an inlet sample port 402 configured to an ionizing chamber 404 that has been evacuated with a vacuum pump (not shown). The ionizing chamber 404 includes an ion source 406 in fluid communication with the sample port 402. The ion source 406 is used to ionize the sample to produce precursor ions. An ion guide 408 is configured within the ionizing chamber 404 to transport the precursor ions from the ion source 406 to a mass analyzer unit 409. In general, the mass analyzer unit 409 is used to separate a fraction of the ions based on a mass-to-charge ratio. In some aspects, the mass analyzer 409 may also be configured to dissociate a portion of the precursor ions into fragment ions. The fraction of ions that passes through the mass analyzer unit 409 may then be transferred to a detector

420. The fraction of ions may be oriented to hit the detector to produce detection signals, as is the case for sector or time-of-flight instruments. While, in some aspects, the fraction of ions may pass near the detection plates to produce the detection signals, as is the case in Fourier transform ion cyclotron resonance mass spectrometry (FT ICR). The detection signals may then be transformed into chromatograph or mass spectra using a data processor 428 and a controller 422.

Suitable samples for the mass spectrometry unit 400 system include macromolecules comprising monomer subunits or small molecules. In one non-limiting example, the sample includes a glycan comprising monosaccharide monomer subunits. A suitable mass analyzer unit 409 may include a first quadrupole mass filter 410, a collision cell 412, and a second quadrupole mass filter 418. In general, the first and second quadrupole mass filters 410, 418 include several rod electrodes which may be configured to receive a predetermined amount of voltage that causes a fraction of ions to separate when passing through the quadrupole mass filters 410, 418. The separation is determined by the mass-to-charge ratio (m/z) of the ions. In general, the collision cell 412 includes a multipole ion guide 414 and a gas supply unit 416 that are configured to impart a collision between incoming precursor ions from the first mass filter 410, and an inert gas to induce further dissociation or fractionation of the precursor ions to produce fragment ions. The multipole ion guide 414 is also configured to receive a predetermined amount of voltage for focusing and controlling the position of the ions within the collision cell 412. The gas supply unit 416 is configured to deliver an inert gas (e.g., nitrogen, helium) into the collision cell 412.

The mass spectrometry unit 400 also includes a controller 422 that may include a display 424, one or more input devices 426 (e.g., a keyboard, a mouse), and a data processor 428. The data processor 428 may include a commercially available programmable machine running on a commercially available operating system. The data processor 428 is configured to be in electrical communication with the detector 420 and the controller 422. The controller 422 provides an operator interface that facilitates entering input parameters into the mass spectrometry unit 400. The controller 422 may be configured to be in electrical communication with several power units, including, for example, a first quadrupole power unit 430, a multiple ion guide power unit 32, and a second quadrupole power unit 434. The first quadrupole power unit 430 is further in electrical communication with the first quadrupole mass filter 410. Similarly, the multipole ion guide power unit 432 and the second quadrupole power unit 434 are in electrical communication with the multipole ion guide 414 and the second quadrupole mass filter 418, respectively. The controller 422 may control the data processor 428, one or more input devices 426, and display 424 to implement similar or the same methods described with reference to FIGS. 2-3.

Under the command of the controller 422, predetermined amounts of voltage may be applied to the first quadrupole power unit 430, the multiple ion guide power unit 432, and the second quadrupole power unit 434. The voltages applied from the first and second quadrupole power unit 430, 434 to the first and second quadrupole mass filters 410 and 418 may comprise radio-frequency voltage added to a DC voltage. The voltage applied from the multiple ion guide power unit 432 to the multiple ion guide 414 may be a radio-frequency voltage. In some aspects, a DC bias voltage is additionally applied to the first and second quadrupole mass filters 410, 418 as well as the multiple ion guide 414.

In operation, a sample is injected into the inlet sample port 402 and is ionized by the ion source 406 to produce precursor ions. The ion guide 408 directs the precursor ions into the first quadrupole mass filter 410. The controller 422 determines the amount of voltage to apply to the first quadrupole mass filter 410, which regulates how many precursor ions are allowed to pass through the first quadrupole mass filter 410 based on a specific mass-to-charge ratio (m/z). A fraction of the precursor ions are subsequently fed into the collision cell 412. The controller 422 determines an amount of voltage to apply to the multiple ion guide 414 to focus and position the ions. The controller 422 then regulates an amount of gas to be introduced from the gas supply unit 416 into the collision cell 412. The gas collides with the ions from the first quadrupole mass filter 410 to produce fragment ions.

The precursor and fragment ions are then passed through the second quadrupole power unit 418, where the ions are filtered a second time. To filter the ions, the controller 422 regulates the amount of voltage delivered to the second quadrupole mass filter 418 to again separate a fraction of the precursor and fragment ions based on a mass-to-charge ratio. The fraction of precursor and fragment ions are then directed to the detector 420 where a detection signal corresponding to the number of each incident ions is produced, and the detection signal is subsequently sent to the data processor 428. The detection signal may be generated by contacting the detector 420, or it may be generated by passing near the detector 420.

The data processor 428 may communicate with the controller 422 to execute stored functions that can create chromatographs and mass spectra based on the data produced from the detection signals by digitizing the signal fed from the mass spectrometry unit 400. The data processor may also perform qualitative and quantitative determination processes based on the chromatograph or mass spectra. Chromatograph or mass spectra data may be conveyed back to the controller 422 where they are stored in data base memory cache, from which they may be transferred to the display 424. In other aspects, the computer system 300 may be integrated into the mass spectrometry unit 400.

In some aspects, the mass spectrometry unit 400 may be configured to acquire a mass spectrum of a molecule that includes mass spectrum peaks corresponding to a precursor ion and fragment ions. The term precursor ion may be produced by using the ion source 306, and the fragment ions may be produced in the collision cell 412 (e.g., O-ion fragments). For example, the macromolecule may pass through the ion source 406 to acquire a charge, or partially fragment and acquire a charge to produce a precursor ion. The precursor ion may then be passed through the collision cell 412 to further dissociate and fragment the precursor ions to produce fragment ions. The mass spectrometry unit 400 may be configured to implement the same or similar methods as described in FIGS. 2-3.

It is to be appreciated that alternative mass spectrometry units may be used in accordance with the present disclosure. In general, any mass spectrometry unit capable of ionizing chemical species and separating them based on their mass-to-charge ratio may be used in accordance with the present disclosure. Suitable examples may include AMS, GC-MS, LC-MS, ICP-MS, IRMS, MALDI-TOF, SELDI-TOF, Tandem MS, TIMS, SSMS, and similar mass spectrometry instruments.

EXAMPLES

The following examples set forth, in detail, ways in which the system may be used or implemented, and will enable one of skill in the art to more readily understand the principles thereof. The following examples are presented by way of illustration and are not meant to be limiting in any way.

Example 1

Figure 5:
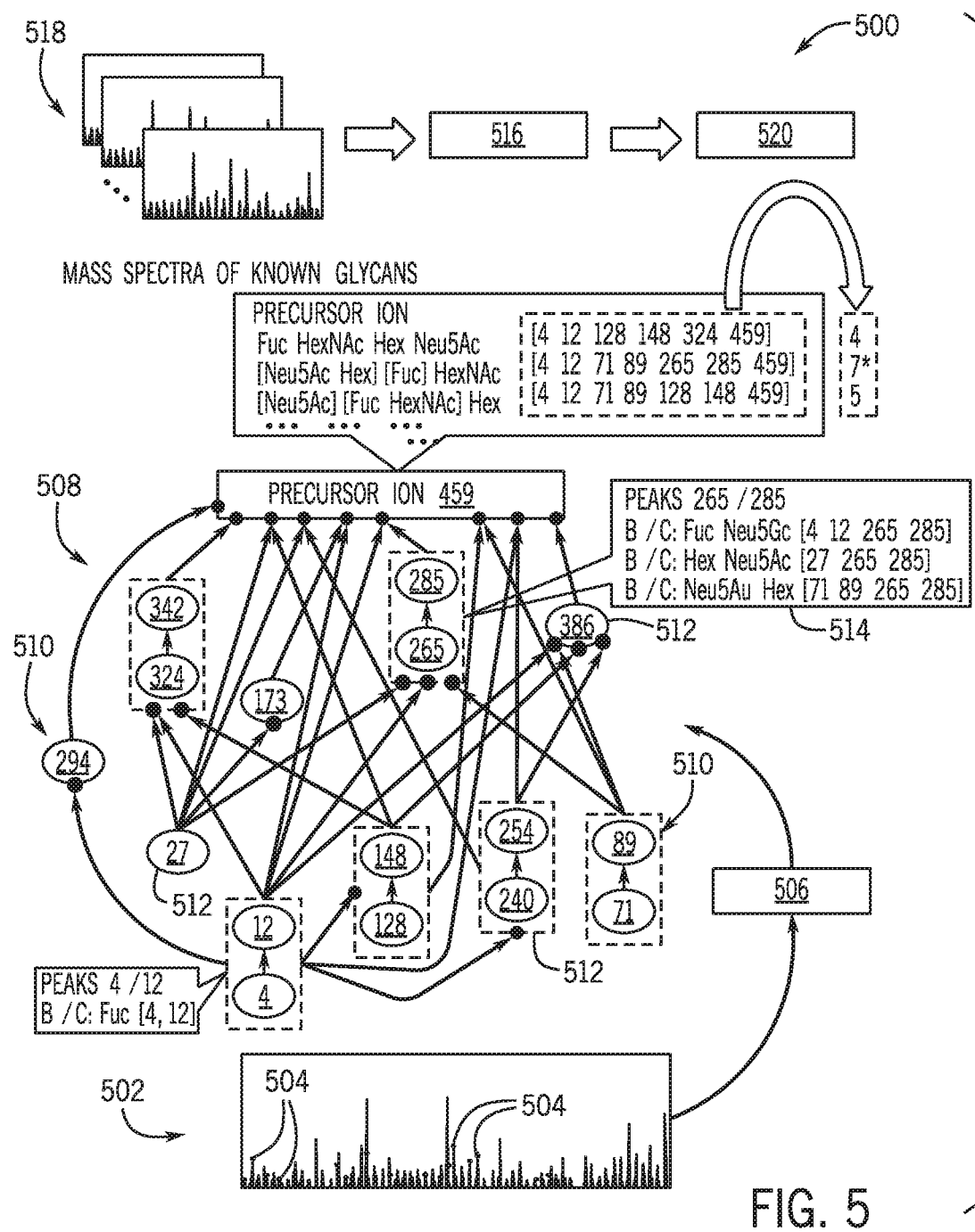
FIG. 5 is a graphical illustration of an example method for determining a topology of a molecule in accordance with one aspect of the present disclosure

FIG. 5 is a schematic flowchart that illustrates a non-limiting example method 500 of determining a topology for a molecule in accordance with the present disclosure. The method 500 includes providing mass spectrum data 502, such as an EED spectrum (SLA), to a computer system. A portion of the fragment ion peaks and the precursor ion peaks were then assigned a peak identification (ID) and a mass-to-charge ratio, as indicated by the dots 504 above the peaks in the mass spectrum 502. These peaks are interpretable by PeakInterpreter 506 to derive the interpretation-graph 508. The interpretation-graph 508 includes multiple identified peaks 510, where the circled numbers inside the interpretation-graph 508 correspond to peak IDs. The interpretation-graph 508 correspond to peak IDs. The interpretation-graph 508 also includes multiple nodes 512 that correspond to a topoReconstruction object (or candidate topology building block) that specifies how the corresponding peak can be interpreted by other peaks pointing to the corresponding peak. The nodes 512 may also include node-pairs as shown in the dashed rounded rectangles, that may be interpreted as B/C-ion pairs. The reconstructed topologies of three peaks (4/12, 265/285, precursor ion) are shown as examples in the rounded rectangle callouts along with their supporting peaks in brackets. This precursor ion has 14 candidate topologies. Based on the supporting peak count, three of them tie for the best and are listed in the call out 514. FIG. 5 also shows an exemplary machine learning 516 that may be applied to automatically learn an IonClassifier 520 to distinguish B and C ions from other ion types using known mass spectra of known glycans 518. IonClassifier 520 may then be used to score topology candidates. In this example, it gives the highest score of 7 to the correct topology [Neu5Ac Hex] [Fuc] HexNAc.

Although GlycoDeNovo can handle glycans containing residue(s) with up to four branches, its performance was tested on bifurcated structures due to the availability of glycan standards. The structures of glycans used in our study are listed in FIG. 7 as Table 1.

Materials

Sialyl lewis A (SLA), sialyl lewis X (SLX), Lewis B, Lewis Y, lacto-N-tetraose (LNT), and lacto-N-neotetraose (LNnT) were purchased from Dextra Laboratories (Reading, UK). Lacto-N-fucopentaose (LNFP) 1, 2, and 3 were acquired from V-LABS, Inc. (Covington, La.). Cellohexaose (CelHex), maltohexaose (MalHex), A2F and NA2F glycans were purchased from Carbosynth Limited (Berkshire, UK). Synthetic N-linked glycan standards (N002 to N233) were obtained from Chemily Glycoscience (Atlanta, Ga.). Man9 N-glycan, $H_2^{18}O$ (97%) water, 2-aminopyridine, acetic acid, dimethyl sulfoxide (DMSO), sodium hydroxide, methyl iodide, chloroform, sodium borodeuteride, and cesium acetate were purchased from Sigma-Aldrich (St. Louis, Mo.). Pierce PepClean C18 spin columns were acquired from ThermoFisher Scientific.

Sample Preparation

For reducing-end $^{18}O$-isotope labeling, each dry native glycan (5 μg) was dissolved in 20 μL of $H_2^{18}O$ to which 2 μL of catalyst solution (2.7 mg/mL 2-aminopyridine in anhydrous methanol) and 1 μL of acetic acid were added. The reaction mixture was incubated at 65° C. for 16 hours. Solvent was removed by a SpeedVac concentrator before permethylation. For deutero reduction, approximately 10 μg each of glycan standards were incubated with 0.5 M sodium borodeuteride in 0.2 M ammonium hydroxide solution for 2 hours at room temperature while mixing, followed by drop-by-drop addition of acetic acid (10%) until bubbling stopped. The reaction mixture was dried down in a centrifugal evaporator. Excess borates were removed by repeated resuspension and drying of the samples in methanol. Permethylation was performed according to the method described previously. Briefly, the underivatized, $^{18}O$-labeled, or deutero-reduced glycan was suspended in 100 μL of DMSO/NaOH solution and gently vortexed for 1 hour at room temperature. Methyl iodide (50 μL) was added to the reaction mixture and the reaction was allowed to proceed for another 1 hour at room temperature in the dark. Additional NaOH/DMSO (100 μL) and methyl iodide (50 μL) were added together followed by 1 hour of vortexing. This process was repeated up to 5 times to ensure complete methylation before the reaction was terminated by addition of 200 μL of chloroform and 200 μL of water. Permethylated glycans were extracted by liquid-liquid fractionation in water and chloroform, and desalted using PepClean C18 spin columns.

Mass Spectrometry Analysis

Permethylated glycans were dissolved to a concentration of 2-5 μM in 50/50 (v/v) methanol/water solution that also contains 20-50 μM of sodium hydroxide or cesium acetate to produce sodium or cesium adducts of permethylated glycans. For electronic excitation dissociation (EED) analysis, each glycan sample was loaded onto a pulled glass capillary tip with a 1-μm orifice diameter and directly infused into a solariX™ hybrid Qh-Fourier transform ion cyclotron resonance (FTICR) mass spectrometer (Bruker Daltonics, Bremen, Germany) equipped with a hollow cathode dispenser. Sodiated or cesiated precursor ions were isolated by the quadrupole mass filter, externally accumulated in the collision cell, and fragmented in the ICR cell by irradiation of electrons for up to 1 second, with the cathode bias voltage set at −14 V and the ECD lens voltage at −13.95 V. Each transient was recorded at a 0.55-s length, and up to 40 transients were summed for improved S/N ratio. Peak picking and deconvolution were achieved with the DataAnalysis™ software (Bruker Daltonics), using the SNAP™ algorithm with the quality factor threshold set at 0.01, S/N threshold set at 2, and maximum charge set at the precursor ion charge state. All tandem MS spectra were internally calibrated with several fragment ions assigned with high confidence to give a typical mass accuracy of <2 ppm.

Results and Discussions

Figure 6:
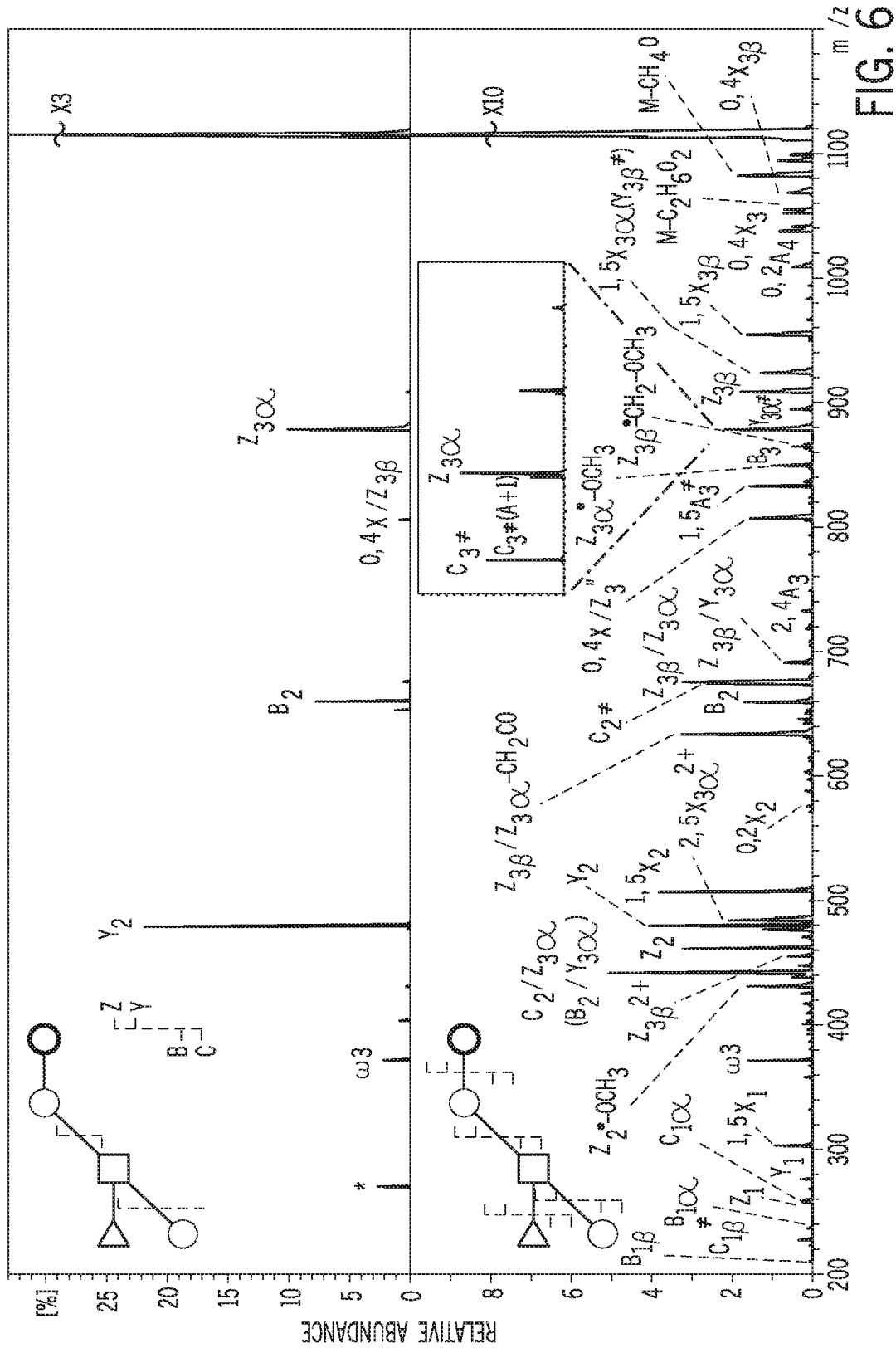
FIG. 6 is an example CID and EED tandem mass spectra of deuteron-reduced and permethylated lacto-N-fucopentaose II (LNFP II, $[M+Na]^+$).

The output accuracy of a computer analysis is intimately tied to the quality of the input data. For the task at hand, the quality of the glycan tandem mass spectral data is characterized by its cleavage coverage and the data ambiguity. Although present disclosure can analyze spectral data with missing cleavage(s) by considering addition of two monosaccharide residues at a time during the peak interpretation and topology reconstruction steps, such a practice may increase the computational time by effectively making |G| larger, while leaving part of the glycan sequence undetermined. Thus, complete sequence determination may include glycosidic cleavage at every linkage site. However, the prevailing glycan fragmentation method to date, collision-induced dissociation (CID), often fails to produce a complete series of glycosidic cleavages. Lately, a number of radical-induced dissociation methods have been applied to structural analysis of glycans, many of which were capable of producing more extensive sequence information than CID. Among them, the recently developed EED is a particularly powerful method, as it can generate rich structural information for glycan characterization, including linkage differentiation, for a wide variety of glycans, with or without derivatization. FIG. 5 is a CID and EED spectra and cleavage maps of deuteron-reduced and permethylated LNFP II, [M+Na]$^+$, with assigned peaks. Whereas CID failed to cleave between the Fuc and GlcNAc residues, and between the reducing-end Gal and Glc residues, EED generated complete sets of B, C, Y, and Z ions. FIG. 6 shows the CID and EED spectra and cleavage maps of deuteron-reduced and permethylated LNFP II, [M+Na]$^+$, with all assigned peaks. Whereas CID failed to cleave between the Fuc and GlcNAc residues, and between the reducing-end al and Glc residues, EED generated complete sets of B, C, Y, and Z ions. Since complete elucidation of glycan topology may include cleavages of all glycosidic bonds, the performance of GlycoDeNovo was initially evaluated on EED spectra of glycan standards.

Data ambiguity can arise from several origins. A common confounding factor in de novo glycan sequencing is the presence of internal fragments that may be misinterpreted as a terminal glycosidic fragment with the same saccharide composition. Permethylation may be a useful strategy for differentiating terminal and internal fragments based on the number of unmethylated "scars" generated by each glycosidic cleavage. Therefore, all glycans analyzed in this example were permethylated before tandem MS analysis. Another challenge is that B and Z ions, as well as C and Y ions, are isomeric if they contain the same set of monosaccharide residues. This symmetry may be broken by $^{18}$O-stable isotope labeling, leading to a mass shift of 2.004 Da for all reducing-end fragments. However, because typical $^{18}$O-labeling conditions can lead to facile loss of sialic acid residues, deutero-reduction was performed as an alternative for glycans containing sialic acid residues, which introduced a 17.038-Da mass shift. A third factor is that glycans are typically analyzed as metal adducts to minimize proton-mediated gas-phase structural rearrangement, yet the number of metal cations in a fragment ion does not always equal to its charge state. Whereas it is possible to expand the peak list by assigning a fragment ion in n+ charge state with either n−1, n, or n+1 (if n is less than the precursor ion charge state) metal cations, this practice not only dramatically increases the computational time by increasing N, but also increases the chance of spurious matches. Since analysis of glycans adducted with a metal cation having a large mass defect can facilitate metal counting, the performance of the present disclosure on EED spectra of both sodiated and cesiated glycans will be evaluated in this example. Finally, glycan tandem mass spectra, especially those generated by EED, can be extremely complex. All experimental data in this example were acquired on an FTICR instrument, as the high mass accuracy measurement it affords is essential for reducing the chance of fortuitous matches due to the presence of isobaric (but not isomeric) fragments.

Topology Reconstruction

The test results for reducing-end modified glycans are summarized in FIG. 8. FIG. 8 includes Table 2 that illustrates of experimental results. All glycans in Table 2 are permethylated. The "REM" column indicates the type of reducing end modifications (O18=18O-labeled, D-R=deutero-reduced, Red=reduced). The "#Peaks" column lists the number of peaks in each enriched spectrum with the number of complementary peaks inside the parentheses. The "#Interpretable" column lists the number of peaks that can be interpreted as B or C ions by PeakInterpreter. The "#Reconstructed" column lists the number of peaks reconstructed by CandidateSetReconstructor. The "#Candidates" column lists the number of reconstructed topology candidates. The "Rank by SPN" and "Rank by IonClassifier" columns list the rank of the true topology among all inferred candidates using their supporting peaks and IonClassifier, respectively. The number inside the parenthesis is the number of other candidates that were ranked the same as the true topology. Highlighted cells indicate improved ranking by IonClassifier.

The number of peaks in the enriched spectrum ranged from 216 to 2683. The percentage of interpretable peaks ranged from ~4.4% to ~23.2%, but the percentage of reconstructed peaks was substantially lower, ranging from ~1% to ~5.7%, because present disclosure only needed to build small interpretation-graphs and reconstruct the topologies of a small number of peaks. These numbers confirmed the computational advantage of the strategy used by the present disclosure to first build the interpretation-graph and delay topology reconstruction after interpreting the precursor ion. For example, the largest peak list (from the EED spectrum of a synthetic N-glycan standard of the hybrid type, N012) contained 2683 peaks with 273 interpretable as non-reducing end glycosidic fragments, only 50 of which needed to be reconstructed.

As the masses used in the present disclosure's algorithm were those of the singly protonated species, the m/z values of peaks found in the experimental spectrum, typically those of metal-adducts, needed to be converted first. To reduce the run time and to minimize spurious matches, we assumed that the number of metal cations in a given fragment is the same as its charge state. Although this may not be the case for all fragment ions, we asserted that the presence of nonconforming fragments would not prevent reconstruction of the correct topology so long as at least one fragment ion produced by each glycosidic cleavage carried the same number of metal cations as its charge state. This appeared to be a reasonable assumption, since the correct topologies were recovered in all cases studied. The nature of the metal charge carriers did not seem to have a major impact on the accuracy of topology reconstruction.

Table 2 is a chart illustrating experimental results where all glycans are permethylated. The "REM" column indicates the type of reducing end modifications (O18=18O-labeled, D-R=deutero-reduced, Red=reduced). The "#Peaks" column lists the number of peaks in each enriched spectrum with the number of complementary peaks inside the parentheses. The "#Interpretable" column lists the number of peaks that can be interpreted as B or C ions by PeakInterpreter. The "#Reconstructed" column lists the number of peaks reconstructed by CandidateSetReconstructor. The "#Candidates" column lists the number of reconstructed topology candidates. The "Rank by SPN" and "Rank by IonClassifier" columns list the rank of the true topology among all inferred candidates using their supporting peaks and IonClassifier, respectively. The number inside the parenthesis is the number of other candidates that were ranked the same as the true topology.

Ultimately, the performance of a de novo glycan sequencing algorithm should be judged by whether it is capable of deducing the correct topology, and how it ranks the correct topology among all candidate structures. As demonstrated by the numbers in the "Rank by SPN (number of supporting peaks)" column in Table 2 in FIG. 8, our approach significantly outperformed all previously reported methods: in most cases, the correct topology was ranked the highest, either by itself, or with a very small number (≤2) of other structures. Such success can be attributed, in part, to the experimental measures taken to reduce data ambiguity, including permethylation, reducing-end isotope labeling, and high-mass-accuracy measurement. It is, however, not always feasible to perform all these procedures experimentally. For example, reducing-end isotope labeling is only applicable towards glycans with a free reducing end, and not suitable for O-linked glycans released via reductive β-elimination that results in a reduced reducing end.

The results presented in Table 2 of FIG. 8 were obtained with the mass accuracy set to 5 ppm, which was considerably higher than the typical mass accuracy (<1-2 ppm) achievable on an FTICR mass analyzer. Nonetheless, the 5 ppm mass tolerance was sufficiently tight for differentiating the mass difference between $CH_4$ and O (0.036 Da), which is the most common cause of isobars in glycan tandem mass spectra. Test results obtained at this mass accuracy appeared to be satisfactory, suggesting that GlycoDeNovo should perform reasonably well on spectral data with moderate mass accuracy, such as those acquired on the more widely available time-of-flight instruments.

Candidate Ranking by IonClassifier

The analysis result of A2F (reduced, $Na^+$-adduct) offers a perfect example to showcase the utility of IonClassifier in candidate ranking. It should come as no surprise that a large number of candidate topologies (990750) were derived by GlycoDeNovo for this 12-residue complex N-glycan (the largest studied here) without a reducing-end label, whose enriched peak list contains 2646 peaks. When ranked by SPN alone, the true topology was placed at the $207,829^{th}$ along with 201169 other candidates. This is because Peak-Interpreter misinterpreted 97 peaks as as B or C ions. For example, the peak at m/z 406.2078 was misinterpreted as a B ion, "Neu5Gc", which was used to support 34,741 candidates ranked higher than the true topology; the peak at m/z 464.2488 was misinterpreted as a B ion, "Hex HexNAc", which was used to support 139,971 candidates ranked higher than the true topology. IonClassifier was able to recognize these peaks as non-B or C ions, and rank the true topology at $1^{st}$ based on the cumulative IonClassifier values of all its supporting peaks. The use of IonClassifier can also boost the ranking of the true topology for glycans with a reducing-end isotope label. For example, ranking by IonClassifier promoted the correct topology of $^{18}$O-labeled Man9 N-glycan ($Na^+$-adduct) from 205th to the 1st rank with four other structures; it also ranked the true topology of every $^{18}$O-labeled LNFP glycan as the top candidate by itself. Notably, this superior performance of IonClassifier was achieved without enforcing biosynthetic rules.

IonClassifier can be very useful for ranking topologies for glycans without any reducing-end modification (including reduction), where misinterpretation of a Y ion as a C ion or a Z ion as a B ion cannot be avoided based on the accurate mass measurement alone. However, the context for a C ion and that for a Z ion are likely different. For example, a C ion may be accompanied by a $^{1,5}A$ ion that is 46.005 Da lighter, whereas a Z ion may be accompanied by a $^{1,5}X$ ion that is 27.995 Da heavier. The topology reconstruction results for glycans without any reducing-end modification are shown in Table 2 of FIG. 8. For symmetric linear structures, such as cellohexaose and maltohexaose, the peak lists for C and Y ion series are identical, so are those for B and Z ion series, thus there is no need to differentiate C and Y or B and Z ion pairs. Consequently, ranking by SPN was sufficient to place the correct topology as the top-ranked candidate by itself. For asymmetric linear structures (e.g. LNT) and branched structures (e.g. SLA), ranking by SPN often resulted in several structures (including the correct one) sharing the top rank due to its inability to differentiate C and Y, or B and Z ion pairs. When ranked by IonClassifier, however, the correct topology was always ranked the highest by itself. This helps to demonstrate that GlycoDeNovo can effectively be applied to analyze non-reducing glycans.

Close inspection showed that IonClassifier could detect meaningful contextual features that were useful for differentiating ion types and identifying fragmentation patterns. For example, distributions of example contextual features that are useful for differentiating B and C ions from Y, Z, or O ion may be generated in a distribution graph. The horizontal axes may indicate if a feature exists in a spectrum: 0=not present; 1=present, while the vertical axes indicate the percentage of a certain type (or types) of ions displaying or missing in a given feature. Some of these features can be easily assigned, e.g. $B_n$−27.9949 ($^{1,5}A_n$), $B_n$+18.0089 ($C_n$), $B_n$+15.9937 ($C_n$−2H), $C_n$−46.0052 ($^{1,5}A_n$), and $C_n$+70.0428 ($^{2,4}A_{n+1}$). IonClassifier also captured some contextual features that were significantly more likely to appear in the context of Y, Z, or O ions than in the context of B or C ions. For example, −46.0052 and +34.0043 were barely observed in the context of B ions, and −14.0152 and +15.9937 appeared scarcely in the context of C ions.

For any given glycan spectrum that was being tested by IonClassifier, it was excluded from being used to train IonClassifier. In addition, only the spectral data of reducing-end modified glycans were used to train IonClassifier. The rationale is that, without any reducing-end modification, many B (or C) ions would have the same mass as Z (or Y) ions, even for asymmetric structures, such as $B_1$ and $Z_1$ ions, as well as $B_3$ and $Z_3$ ions, of LNT and LNnT. Because the contexts of isomeric B and Z, or C and Y ions, are essentially the same, inclusion of these spectral data for training would only serve to misguide the training of IonClassifier. Nonetheless, the IonClassifier learned from the spectral data of modified glycans appeared to work well for unmodified glycans (see the last 3-7 rows of Table 2). This is perhaps not surprising as one would not expect the reducing-end isotope-labeling to significantly alter the glycan fragmentation pattern. Naturally, presence of similar structural motifs in the training dataset can boost the performance of IonClassifier. Thus, the accuracy and robustness of IonClassifier can be further improved as more experimental data become available for training.

CONCLUSIONS

The present disclosure provides an efficient and robust algorithm for accurate reconstruction of glycan topologies from their tandem mass spectra. It uses an efficient strategy with a polynomial time complexity to reconstruct candidate topologies. In addition, present disclosure is equipped with a machine-learning based IonClassifier for candidate topology scoring. The experimental results clearly demonstrated the power of GlycoDeNovo and IonClassifier for de novo glycan sequencing. The present study showed that it is possible to automatically learn fragmentation patterns from real-world tandem MS data.

The present disclosure has described one or more preferred embodiments, and it should be appreciated that many equivalents, alternatives, variations, and modifications, aside from those expressly stated, are possible and within the scope of the invention.

I claim:

1. A method for determining a topology for a molecule using a mass spectrometer, the method comprising:
   a) acquiring a mass spectrum of a molecule, the mass spectrum including mass spectrum peaks corresponding to a precursor ion and fragment ions, wherein the precursor ion corresponds to an ionized product of the molecule and the fragment ions correspond to dissociated products of the molecule;
   b) identifying at least a portion of the fragment ions in the mass spectrum as corresponding to one or more monomer subunit ion of the precursor ion, wherein the one or more monomer subunit ion is identified by appending one or more of the fragment ions to an inferable constituent to produce a topology building block, and storing the topology building block in a candidate pool as corresponding to one or more of the monomer subunit ion if the combined mass of the inferable constituent and one or more of the fragment ions satisfy a first user-defined mass tolerance; and
   c) reconstructing one or more candidate topology of the precursor ion by combining a plurality of the topology building blocks that satisfy a second user-defined mass tolerance for the precursor ion,
   wherein the one or more monomer subunit ion comprises a B ion glyosidic fragment or C ion glyosidic fragment, and the inferable constituent is a monosaccharide, and wherein step b) further includes identifying the portion of fragment ions in the mass spectrum as corresponding to B ion glycosidic fragments or C ion glycosidic fragments by attaching up to four branches to the monosaccharide, and wherein the branches are interpretations of fragment ion peaks that are lighter than the one being interpreted.

2. The method of claim 1, further comprising selecting a topology for the precursor ion by ranking the one or more candidate topology based on a candidate topology score, and selecting the candidate topology with the highest candidate topology score.

3. The method of claim 1, wherein the molecule comprises a glycan, the precursor ion comprises a glycan ion, and the one or more monomer subunit ion comprises a glycosidic fragment.

4. The method of claim 1, wherein the one or more monomer subunit ion a non-reducing end glycosidic fragment.

5. The method of claim 1, wherein the inferable constituent comprises a monosaccharide.

6. The method of claim 1, wherein step b) further includes computationally adding artificial mass spectrum peaks to compensate for a portion of the fragmentation ions that are unobservable in the experimental spectrum due to a lack of charge carrier or secondary fragmentation.

7. The method of claim 1, wherein combining the one or more monomer subunit ion with the inferable constituent includes attaching up to four branches of the monomer subunit ion to the inferable constituent to obtain the candidate pool of one or more topology building block that satisfies the first user-defined mass tolerance.

8. The method of claim 7, wherein the branches include the one or more topology building blocks that correspond to lighter mass spectrum peaks than the mass spectrum peak being interpreted.

9. The method of claim 1, further comprising selecting a topology for the molecule by applying machine-learning to generate a candidate topology score based on a likelihood that the fragment ions in the mass spectrum correspond to the one or more monomer subunit ion identified in the candidate pool, and selecting the one or more candidate topology with the highest candidate topology score as the topology for the precursor ion.

10. The method of claim 2, wherein generating the candidate topology score includes defining a mass difference window in the mass spectrum that includes one or more of the fragment ions, and expressing the fragment ions as an array of contextual features to determine if the fragment ions in the mass difference window correspond to a monomer subunit ion.

11. The method of claim 10, wherein a positive value is assigned to fragment ions that contain the highest likelihood of corresponding to a monomer subunit ion based on the array of contextual features, and a negative value is assigned to mass spectrum peaks that contain the lowest likelihood of corresponding to a monomer subunit ion based on the array of contextual features.

12. The method of claim 8, wherein the mass-difference window is approximately 105 Da.

13. The method of claim 1, wherein the first user-defined mass tolerance and the second user-defined mass tolerance are 0.02 Da or less.

14. A mass spectrometry unit comprising:
   an inlet port configured to receive a sample that includes a macromolecule comprising monomer subunits;
   an ion source configured to ionize the sample to produce a precursor ion, the precursor ion having a first mass-to-charge ratio;
   a mass analyzer configured to dissociate a portion of the precursor ion to produce fragment ions, the mass analyzer configured to separate a fraction of the precursor ion and the fragment ions;
   a detector configured to produce detection signals corresponding to the fraction of the precursor ion and the fragment ions;
   a controller configured to receive the detection signals, the controller programmed to:
      a) acquire a mass spectrum of a molecule, the mass spectrum including mass spectrum peaks corresponding to a precursor ion and fragment ions, wherein the precursor ion corresponds to an ionized product of the molecule and the fragment ions correspond to dissociated products of the molecule;
      b) identify at least a portion of the fragment ions in the mass spectrum as corresponding to one or more monomer subunit ion of the precursor ion, wherein the one or more monomer subunit ion is identified by appending one or more of the fragment ions to an inferable constituent to produce a topology building block, and storing the topology building block in a candidate pool as corresponding to one or more of the monomer subunit ion if the combined mass of the inferable constituent and one or more of the fragment ions satisfy a first user-defined mass tolerance; and
      c) reconstruct one or more candidate topology of the precursor ion by combining a plurality of the topology building blocks that satisfy a second user-defined mass tolerance for the precursor ion, wherein the one or more monomer subunit ion comprises a B ion glyosidic fragment or C ion glyosidic fragment, and the inferable constituent is a monosaccharide, and wherein step b) further includes identifying the portion of fragment ions in the mass spectrum as corresponding to B ion glycosidic fragments or C ion glycosidic fragments by attaching up to four branches to the monosaccharide, and wherein the branches are interpretations of fragment ion peaks that are lighter than the one being interpreted.

15. The mass spectrometry unit of claim 14, wherein the controller is further programmed to: select a topology for the precursor ion by ranking the one or more candidate topology based on a candidate topology score, and selecting the candidate topology with the highest candidate topology score.

16. The mass spectrometer of claim 14, further comprising a display, wherein step b) further includes generating an interpretation-graph that graphically illustrates the one or more candidate topology building blocks.

17. The mass spectrometer of claim 14, wherein the molecule comprises a glycan, the precursor ion comprises a glycan ion, and the one or more monomer subunit ion comprises a glycosidic fragment.

18. The method of claim 1, wherein the inferable constituent comprises a monosaccharide.

19. A method for determining a topology for a molecule using a computer system, the method comprising:
   a) providing an acquired mass spectrum of a molecule to a computer system, the mass spectrum including mass spectrum peaks corresponding to a precursor ion and fragment ions, wherein the precursor ion corresponds to an ionized product of the molecule and the fragment ions correspond to dissociated products of the molecule;
   b) identifying, using the computer system, at least a portion of the fragment ions in the mass spectrum as corresponding to one or more monomer subunit ion of the precursor ion, wherein the one or more monomer subunit ion is identified by appending one or more of the fragment ions to an inferable constituent to produce a topology building block, and storing the topology building block in a candidate pool as corresponding to one or more of the monomer subunit ion if the combined mass of the inferable constituent and one or more of the fragment ions satisfy a first user-defined mass tolerance; and
   c) reconstructing, using the computer system, one or more candidate topology of the precursor ion by combining a plurality of the topology building blocks that satisfy a second user-defined mass tolerance for the precursor ions,
wherein the one or more monomer subunit ion comprises a B ion glyosidic fragment or C ion glyosidic fragment, and the inferable constituent is a monosaccharide, and wherein step b) further includes identifying the portion of fragment ions in the mass spectrum as corresponding to B ion glycosidic fragments or C ion glycosidic fragments by attaching up to four branches to the monosaccharide, and wherein the branches are interpretations of fragment ion peaks that are lighter than the one being interpreted.

* * * * *